United States Patent
Hargett et al.

[11] Patent Number: 5,230,865
[45] Date of Patent: Jul. 27, 1993

[54] VENTABLE RUPTURE DIAPHRAGM-PROTECTED CONTAINER FOR HEATING CONTAINED MATERIALS BY MICROWAVE RADIATION

[75] Inventors: Wyatt P. Hargett, Matthews; Sara E. Littau, Charlotte, both of N.C.

[73] Assignee: CEM Corporation, Matthews, N.C.

[21] Appl. No.: 948,134

[22] Filed: Sep. 21, 1992

Related U.S. Application Data

[63] Continuation of Ser. No. 404,693, Sep. 8, 1989, abandoned.

[51] Int. Cl.[5] ............... B01L 3/00; G05D 16/08
[52] U.S. Cl. .................... 422/102; 422/78; 422/103; 422/113; 219/10.55 E; 220/89.2; 220/207; 220/367
[58] Field of Search .............. 422/78, 99, 102, 103, 422/112, 113; 219/10.55 E, 10.55 M; 220/89.2, 89.1, 206, 207, 209, 366, 376

[56] References Cited

U.S. PATENT DOCUMENTS

| | | | |
|---|---|---|---|
| 2,924,354 | 2/1960 | Hansen | 220/89.2 |
| 3,080,091 | 3/1963 | Philip | 220/89.2 |
| 4,151,253 | 4/1979 | Waggoner | 422/68 |
| 4,248,831 | 2/1981 | Hughes | 422/102 |
| 4,590,957 | 5/1986 | McFarlane | 220/89.2 |
| 4,613,738 | 9/1986 | Saville | 219/10.55 R |
| 4,672,996 | 6/1987 | Floyd | 137/522 |
| 4,736,083 | 4/1988 | Saville | 219/10.55 R |
| 4,877,624 | 10/1989 | Floyd et al. | 219/10.55 R X |
| 4,882,128 | 11/1989 | Hukvari et al. | 422/119 |
| 4,904,450 | 2/1990 | Floyd | 422/113 |
| 4,933,529 | 6/1992 | Saville | 422/113 X |
| 4,944,923 | 7/1990 | Heinrichs et al. | 422/102 |

Primary Examiner—James C. Housel
Assistant Examiner—Jeffrey R. Snay
Attorney, Agent, or Firm—Raymond F. Kramer

[57] ABSTRACT

A ventable container for materials to be heated (preferably digested) by microwave radiation includes a movable rupture diaphragm in a venting passageway in a closure or cover for such container. Such diaphragm is tightenable into place so that the container is sealed and in such sealed state is protected by the rupture diaphragm against pressures that could develop in the container that are higher than that for which it was designed. An important feature of the invention is that the rupture diaphragm is controllably movable, when desired, to open positions to vent the container during heating and afterward, and is resealable after such venting. Because of the chemical reactivity of the reagents utilized in digestions an inner chemically resistant liner is desirably employed in conjunction with a physically stronger outer body, with the outer body giving the liner enough strength to withstand pressures developed during the heating. Also within the invention are processes for heating and digesting materials in the described containers with microwave radiation, microwave heating apparatuses including the invented containers, and lined containers wherein the liners are of improved sealing structures so that the containers are more tightly sealed when heated.

10 Claims, 6 Drawing Sheets

VENTABLE RUPTURE DIAPHRAGM-PROTECTED CONTAINER FOR HEATING CONTAINED MATERIALS BY MICROWAVE RADIATION

This is a continuation of application Ser. No. 07/404,693, filed Sep. 8, 1989 now abandoned.

This invention relates to containers suitable for holding materials to be heated by microwave radiation. More particularly, it relates to ventable containers which include rupture diaphragms and which are especially useful for holding analytical samples which are being digested by treatments with strong chemicals, such as nitric, hydrochloric and sulfuric acids. In such heatings and digestions it is often important to keep the digestion vessel sealed to prevent contamination and to prevent losses of materials and reaction products. As heating and digestion proceed the internal pressure of the container normally increases as material therein is vaporized. To prevent damage to the container by any development of excessive pressure a rupture diaphragm is provided to vent vessel gas at a pressure lower than that which will cause significant damage to the container (and possibly to operators using it). By means of the present invention the intact rupture diaphragm is movable to al venting of the container at the conclusion of the digestion, which facilitates earlier opening of the container and removal of the digested materials without the danger of sudden release of contents through the container opening when the container pressure is suddenly dropped to atmospheric as the closure is removed. Also, the rupture diaphragm may be moved or may be allowed to move during the digestion operation to maintain a desired pressure and temperature profile during such process. Such movement is controllable so that the exit of gases from the container can be controlled, and the closure is resealable after ventings.

The invention also relates to a closure for a digestion container, which closure contains a venting passageway and a rupture diaphragm in the passageway. Such closure may also include a pressure tap connected to a monitor or a controller, and in another embodiment of the invention such tap may be in a fitting adapted to fit the closure, which fitting contains a communicating venting passageway and the rupture diaphragm from the closure.

Also within the invention are various heating and digestion processes which utilize the invented containers or ones that are similar. Another aspect of the invention is an improved seal between a strengthening container body, a liner and a top closure for the container, which seal tightens at elevated temperature.

Microwave powered heating digestions of various materials utilizing strong digesting agents, such as acids, are known and open vessel digestions of this type are described in 47 *Analytical Chemistry* 1475 (A. Abu Samra et al., 1975) and 50 Analytical Chemistry 1021 (P. Barrett et al., 1978). Closed system microwave digestions have also been practiced, as reported in 56 Analytical Chemistry 2233 (Nadkarni, 1984) and in Bureau of Mines Technical Progress Report No 120 (S. A. Matthews et al., 1983). Savillex Corporation has marketed a lidded digestion vessel for microwave digestions which is made of Teflon ® PFA, obtainable from E. I. DuPont de Nemours, Inc., and CEM Corporation has marketed pressure controlling acessories for use in microwave digestions in conjunction with its MDS-81 and MDS-81-D microwave systems.

U.S. Pat. No. 4,672,996 describes a relief valve for use on a container for material being digested in a microwave apparatus, and other relief valves are disclosed in U.S. Pat. Nos. 4,400,401; 4,474,211; and 4,493,444. To protect against the sealed digestion container being harmed (or even exploded) by a run-away digestion reaction which develops excessive pressure, a lined container inside a strengthening container body, equipped with a threaded cap to hold a closure onto the liner, has been marketed, which includes an internal rupture disc. However, such rupture disc is not part of a relief valve or controllable venting mechanism which allows venting past the rupture disc when desired, such as during the digestion process or shortly after its completion, the prior art container does not include improved means for sealing a cover member to the container liner, and the container assemblage does not include an adapter that is useful in monitoring of pressures in the containers or in controlling ventings. Neither does any such prior art or publicly used device teach desired screw or fluid pressure (sometimes in response to a programmed controller) actuated venting of digestion container gas past an intact rupture diaphragm.

In accordance with the present invention a ventable container that is protected by rupture means against possible damaging effects of pressures higher than those for which the container was designed to be held at given temperature comprises radiant energy transmissive container body means for holding material to be heated by radiant energy, which body means comprises an opening for addition and removal of said material, closure means for sealing said container opening, and venting means for venting gas from the container, which venting means comprises a passageway for gas being vented from the container, which passageway terminates in an outlet, rupture means, seating means for the rupture means, against which seating means the rupture means is held, to close the venting passageway, and means for releasably holding the rupture means against the seating means to seal off the venting passageway and the container when the intact rupture means is held against the seating means, and for venting the container through the venting passageway and outlet, when the rupture means is released from the seating means, in which occurrence and when the rupture means ruptures, vented gas exits from the container through the passageway outlet. A shorter description of the invention, in a generalized aspect thereof, is: a container or other apparatus which is protected against damage due to excessive internal pressure, which comprises a container or apparatus, rupture means, which is releasably positioned to seal off a venting passageway to prevent venting from the container or apparatus and release of normal internal pressure, and is movable without rupturing from such sealing location to vent the container or apparatus through the venting passageway and out a passageway outlet, which is the outlet through which gas is vented when the rupture means is ruptured. Preferably the container body means includes a chemically resistant liner inside a strengthening container body and the radiant energy is microwave radiation which is applied to the container of material to be digested or otherwise heated inside the chamber of a microwave heating apparatus. Among significant advantages of the invention are the controllable ventings of the container during and after digestions and the pressure-tight resealability of the closure after ventings.

The invented container, processes for employing it, adapted apparatuses in which the container is used, and sealing structures which may be incorporated in it will be readily understood by reference to this specification and the following description, taken in conjunction with the drawing, in which.

Figure 1:
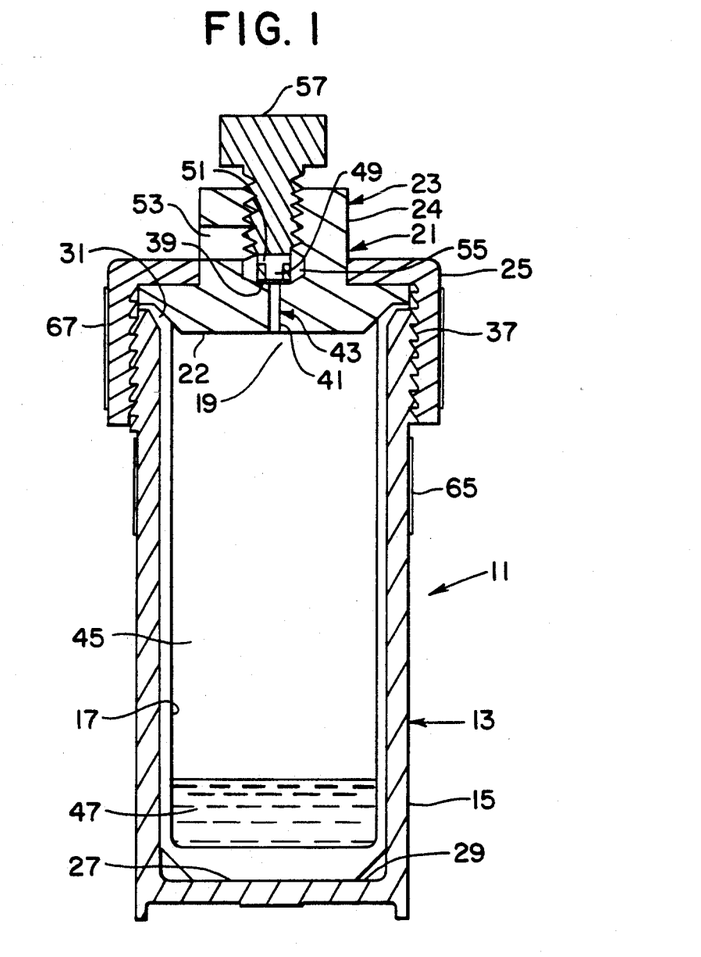
FIG. 1 is a central vertical sectional elevational view of a container of this invention, in a sealed position.

In FIG. 1 there is shown ventable digestion container 11 which comprises container body means or container body 13 (which preferably is of two parts, a body 15 and a liner 17, as illustrated, each of which is of substantially cylindrical, bottomed construction which container has an opening 19 at the top thereof which is closed by closure means 21 (which includes closure portion 23 and holding collar 25). Closure portion 23 includes sealing section 22 and boss 24. Body 15 is of a material of construction which is essentially transparent to microwave radiation and of sufficient strength (tensile strength) and other physical characteristics, including dimensions, so that it can withstand internal pressures in ranges likely to be encountered in various heating and digestion operations in which the container may be employed. Such pressure ranges will normally be from 7 to 35 kg./sq. cm., most often being in the ranges of 7 or 14 to 21 kg./sq. cm. (all pressure readings given in this specification are gauge pressures, meaning that to obtain absolute pressures one must add one atmosphere or about one kg./sq. cm.). Most suitable synthetic organic polymeric plastic material for such body 13 are any of the polyether imides, such as those sold under the ULTEM ® trademark by General Electric Corporation, but others of the "engineering plastics", fiber reinforced plastics, such as glass fiber reinforced polyesters or polyethers, or other polymers known to be of good strengths and transmissive of microwaves may also be used. Inside body 15, as a part of the container body means 13, is liner 17, which is essentially or completely transparent to microwave radiation and is also resistant to damage from chemical attack by strong chemicals, such as strong acids, often employed to digest analytical samples. Materials of construction suitable for manufacture of such liners, such as fluorinated alkylenes or perfluorocarbons, e.g., polytetrafluoroethylene and other polymers of this type sold under the tradename TEFLON ® or other tradenames may be employed, with the preferred materials being TEFLON PFA and TEFLON FEP, but other chemically resistant plastics, such as chloroprene, silicone, ethylene, propylene and other suitable polymers, under the proper circumstances, may also be employed. However, at elevated temperature, such polymers and others which are satisfactorily resistant to chemical reactions with the materials being heated or by the digestion mixes are not usually sufficiently strong to resist pressures that may be developed in the container and therefore such are normally employed only as liners within strengthening body members which are made of other, stronger materials. If microwave- and other radiant energy-transmissive materials that are available or may become available are satisfactorily resistant to chemical damage from the contained materials and are strong enough to resist pressures developed during the heatings of such materials in the closed container the container body means may be made of one piece of one material, without the need for a separate liner. However, at present it appears that in the preferred form of the present invention such separate liner and a strengthening container body will usually be employed together. It will be noted that the bottom 27 of liner 17 is in contact with the interior bottom 29 of the strengthening body part 15. Also, it will be noted that at the top of liner 17, which defines opening 19, the liner includes a portion 31 which is tapered upwardly and outwardly between the top of the cylindrical wall 33 of the liner and the top peripheral portion or flange 35 thereof. It will also be noted that the parts of the strengthening body and the closure which contact the tapered or wedge shaped portion 31 of the liner are shaped accordingly. The primary reason for such construction is to improve the seals between the strengthening body, liner and closure members.

Figure 2:
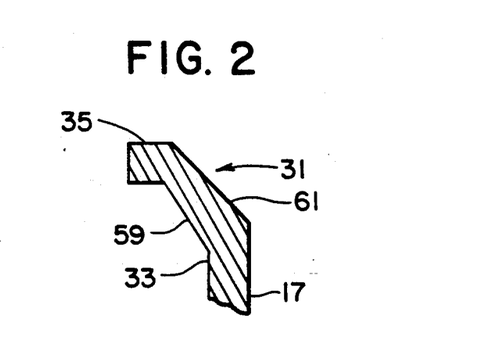
FIG. 2 is an enlarged view, in sectional elevation, of the tapered upper sealing portion of the container liner of FIG. 1.

In FIG. 2 there are shown the angles made by the sides 59 and 61 of tapered liner portion 31. As illustrated, side 59 is about 30° from the vertical and side 61 is about 45° from both the vertical and the horizontal. These angles may be modified so long as a suitable wedge structure is maintained but preferably the angle between the forces will be within the range of 10° to 25°. Flange portion 35 is desirable but in some circumstances may be omitted.

Atop the container, as illustrated in FIG. 1 is closure means 23, which may be held to body means 13 by a suitable holding means, which, in the embodiment illustrated, is threaded collar 25, which screws onto threads 37 on the upper part of body 15.

A venting means is provided for the container and, in the broader aspect of the present invention may be suitably located anywhere on the upper portion of body member 13 but in the illustrated preferred embodiment it is incorporated in and coacts with the closure. In fact, rupturable diaphragm 39, in normal intact state, acts to seal off upstream portion 41 of the venting passageway 43. If rupture disc 39 is ruptured, due to a high internal presssure in the container 13, gas 45 inside the container, generated by vaporization of heated material or digestion mixture 47, will vent from the container through upstream passageway 41, through ruptured disc 39, through vertical downstream passageway 49 (which is of greater diameter than passageway 41), through horizontal transverse passageways 51 and through clearances 55, and out venting passageway outlet (or outlet) 53. It will be noted that if rupture disc 39 ruptures the venting gas will exit through passageways 41, 49, 51, and 55 and outlet 53, in that order, whereas if (as will be discussed later) the rupture disc is moved from sealing contact so that it no longer seals off passageway 41 (or 43) the gas may exit primarily through passageways 41 and 55 and outlet 53. Passageway outlet 53 may be connected by tubing (not shown in FIG. 1) or other means to another container, to an exhaust fan inlet or to the exterior of the microwave apparatus, if desired.

As illustrated in FIG. 1, closure means 21 includes the described passageways in sealing (lower) and boss (upper) portions thereof and the boss portion is internally threaded to receive a threaded stem or tightening member 57. Stem 57 may be tightened down so as to peripherally (around opening 49) press rupture diaphragm 39 against a contacting lower seat in the closure member, to seal off passageway 43. In such sealing position the container is protected against high pressure explosions by the rupture disc 39 and the rate of release of venting gas can be regulated by changing (restricting or enlarging) the diameter of passageway 41, as well as by changing the dimensions of other parts of the venting passageway 43, to prevent too rapid a discharge of container contents, or to facilitate such discharge. When threaded stem 57 is backed off gas may be released from apparatus 11 at below the rupturing pressure (or force) for the rupture disc. Such release of pressure or venting is usually very desirable at the end of a digestion process because otherwise it will be necessary to cool the container to a temperature at which the internal pressure equals that of the atmosphere, before the closure may be removed and the digested material may be discharged so a to be further processed or analyzed. By utilizing the "discretionary" venting provision of this invention considerable time and cooling effort will be saved because the venting allows faster equalization of the internal pressure with that of the atmosphere and thereby enables the chemist or operator to remove the closure without fear of it being released too rapidly and without fear that contents will be lost, due to boiling, bubbling or bumping upon sudden pressure release, with consequent entrainment in the vented gas. When organic materials are being digested there will be an increase of pressure in the digestion container due to reactions which result in gaseous products, so even when the container is cooled in an ice bath after completion of digestion considerable pressure could remain in the container, making it hazardous to remove the closure in the absence of venting means.

Figures 3, 4:
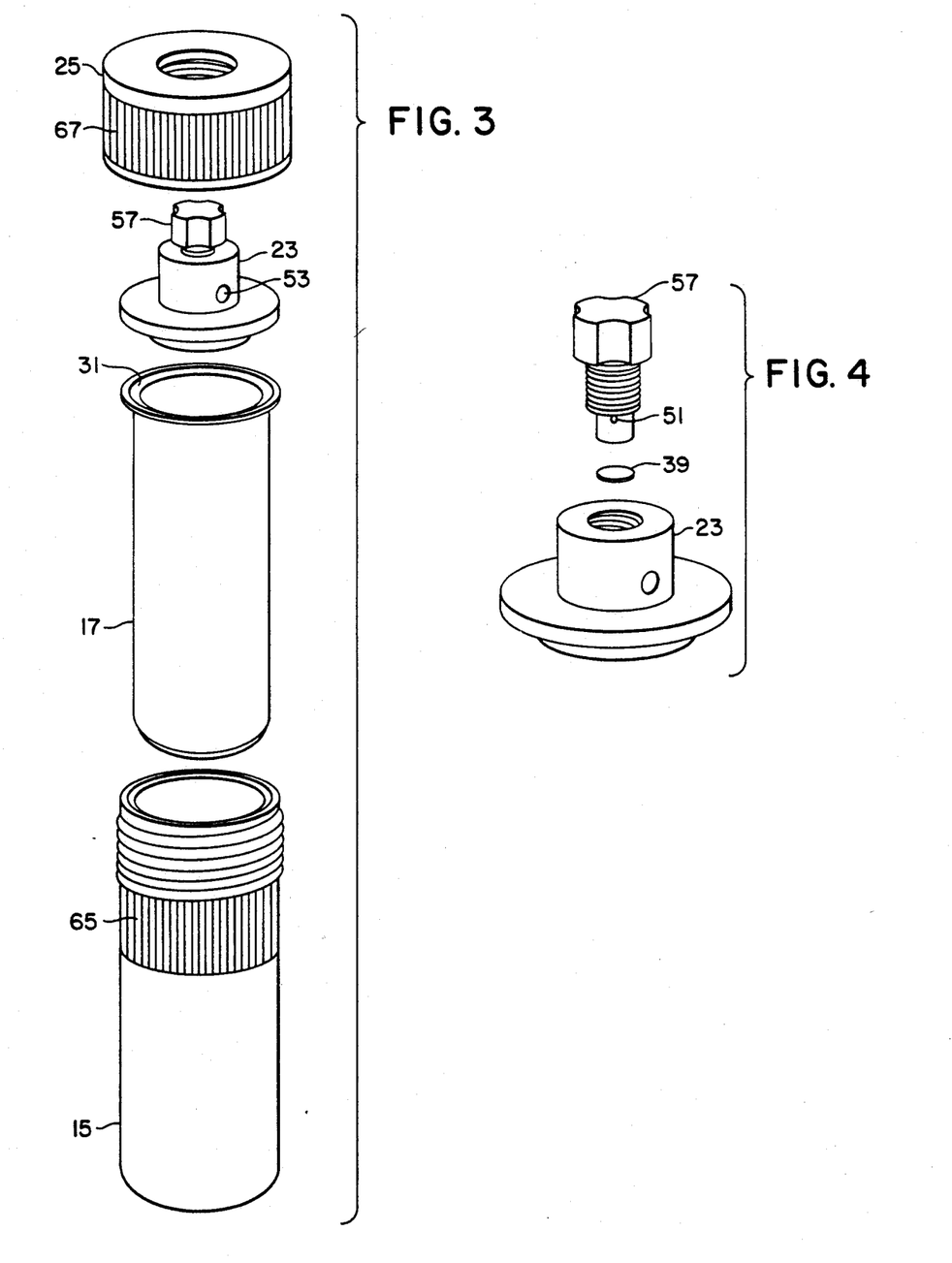
FIG. 3 is a partially disassembled view of the components of the container of FIG. 1.
FIG. 4 is another disassembled view of some of the components of the closure shown in FIGS. 1–3.

In FIGS. 3 and 4 are shown various parts of the assembled container of FIG. 1 so except for a few details no further discussion of these figures and such parts is required. However, it should be noted that because of the tight seals obtained between the container body, liner and closure, a highly preferred form of which seal is shown in FIG. 1, it is not necessary to utilize mechanical equipment, such as a torque wrench, in the assembly of the container. Ridges 67, on cap 25, and 65, on body 15, provide sufficient gripping surfaces so as to facilitate hand tightening, which satisfactorily holds the container parts in sealing engagement, even at elevated temperature, which was not possible with "ordinary" seals.

Figure 5:
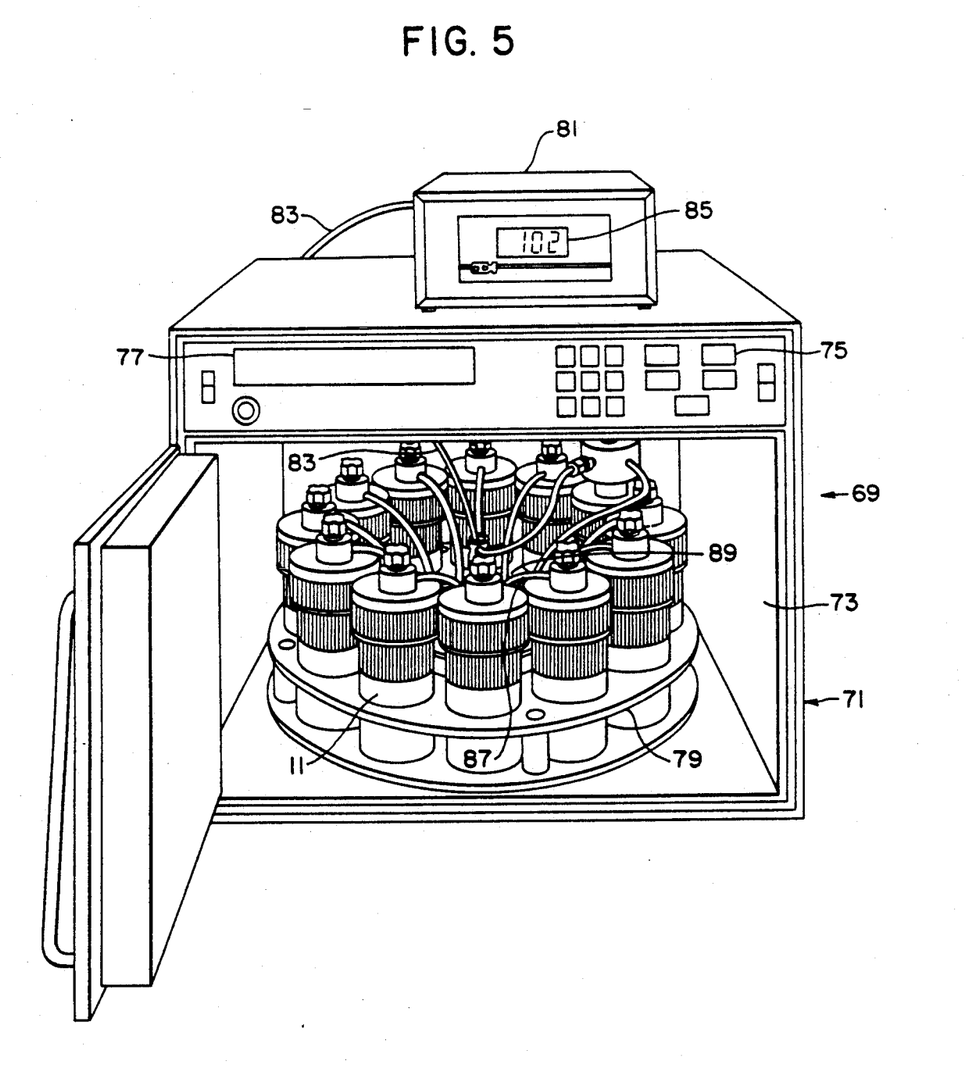
FIG. 5 is a perspective view of a microwave apparatus equipped with a turntable on which are positioned a plurality of containers of this invention.

In FIG. 5 is shown microwave system or apparatus 69 which comprises a housing 71 which defines a heating chamber 73 and which includes a source of microwave radiation (a magnetron), not shown, means 75 for setting microwave power and duration cycles, and display means 77. Such are essentially the same as those of the MDS-81-D microwave digestion apparatus marketed by CEM Corporation, and therefore do not have to be described in further detail. Inside the microwave chamber 73 is a turntable 79 in which are positioned a plurality of microwave transparent digestion containers 11 of this invention. Such containers and their relationship to the turntable, a container for receiving vented materials from the digestion containers, and an adapter for use in monitoring and controlling pressure buildups in the containers are shown in more detail in FIG. 6. Tube 83 transmits pressure from one of the digestion containers to a monitor and/or controller 81, which indicates the pressure on visual display 85, and may regulate microwave energy delivered to maintain the pressure at optimum level(s). Similar temperature monitors and/or controls may also be present. Tubes 87 transmit vented gas (and any entrained droplets of liquid) to collecting container 89 from container vents 53. The gas may be vented from the collector and the liquids (if any) may be recovered from it.

Figure 6:
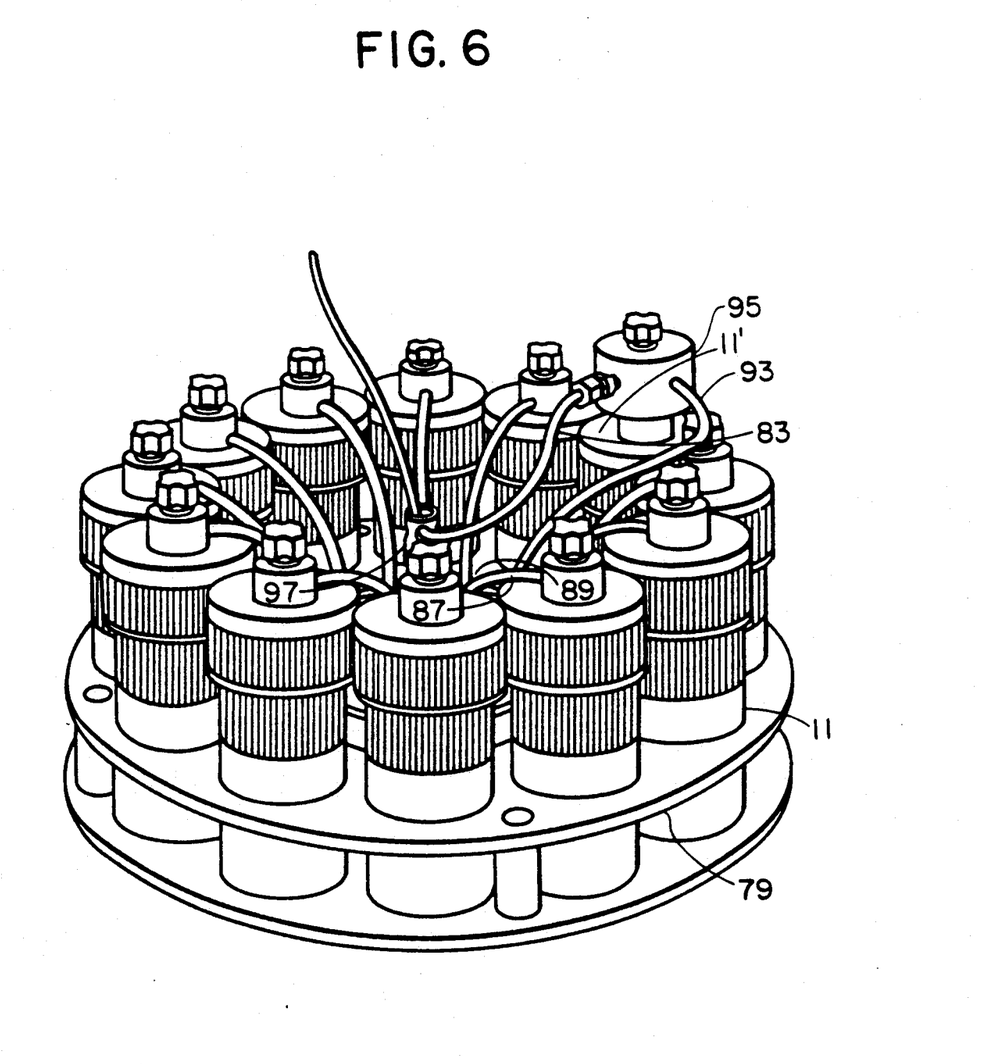
FIG. 6 is an enlarged perspective view of a plurality of containers of FIG. 1 on a turntable, showing an adapter on one container for connection to a pressure monitor and/or controller.

In FIG. 6 there are illustrated five digestion containers 11 and a modified digestion container 11' in the turntable 79, with venting connections or tubes 87 for transfer of vented gas from the containers to the collecting container 89, which minimizes liquid loss. Tube 93 delivers any vented gas from container 11' to container 89 but is connected to container 11' through adapter 95, which will be described in detail with reference to FIG. 7. The purpose of discharging vented gases from the digestion vessels to container 89 is to minimize any discharges of aspirated liquid (which is often corrosive) onto the microwave apparatus container and turntable parts. Vented gas, separated from any entrained liquid droplets, can vent into the microwave apparatus chamber interior, from which it is withdrawn by a conventional exhaust fan or blower, not shown. Tube 83 transmits the internal pressure of container 11' to monitor/controller 81. Such tube is threaded through openings in tubular spindle 97 and from there is connected to the monitor/controller. It will be evident that because of the connection of tube 83 to monitor/controller 81 turntable 79 cannot revolve, but must oscillate. Such oscillating movement is important to provide essentially the same microwave power to each of the containers of material being digested so that they will all be heated at about the same rate (when the same types of heatings for digestions are being undertaken). When the containers and contents are evenly heated it becomes possible for a single pressure and/or temperature probe in one of the containers to replace similar probes in all the containers. Thus, only one adapter needs to be fitted onto one container to obtain a pressure or temperature reading and on the basis of that reading the power to the magnetron and the microwave radiation from it may be adjusted automatically either to heat the digestion mixture or to slow down or halt the rate of heating, to keep the pressure and/or temperature within the desired limits.

Figure 7:
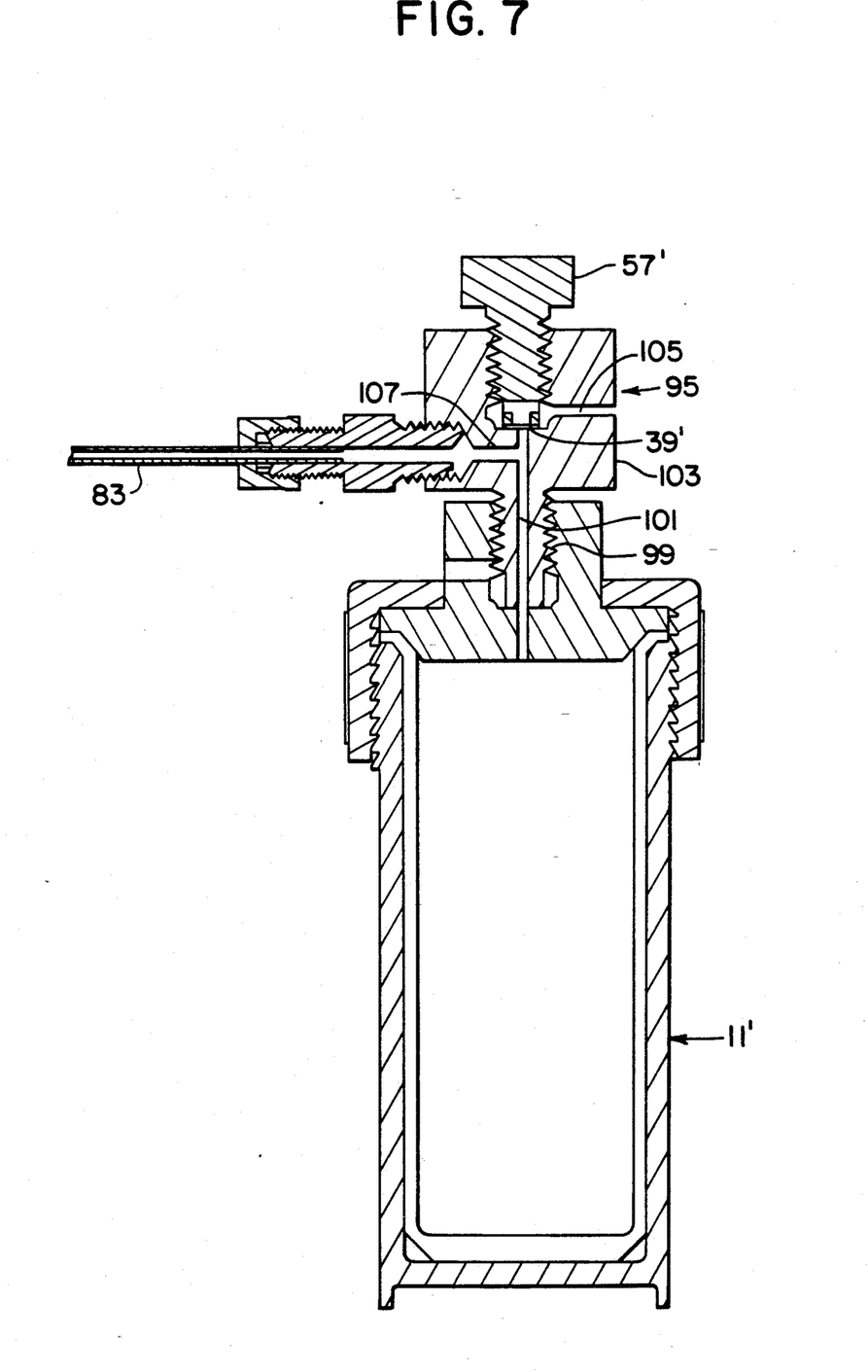
FIG. 7 is a central vertical sectional elevational view of a container of the invention like that of FIGS. 1–4 but equipped with an adapter that is connected to a pressure monitor or controller.

In FIG. 7 container 11' is shown with "adapter" 95 screwed into it so as to provide a tap in the adapter for transmitting container pressure to a monitor/controller or other suitable device, while at the same time providing rupture diaphragm protection against excessive pressures in the container. The adapter is designed to fit the closure of container 11 (or 11') when that closure has removed from it the rupture diaphragm and threaded stem 57. Adapter 95 includes a threaded portion 99 having a hollow bore 101 in it that extends into a body portion 103 of the adapter in which there is a seat below rupture disc 39', against which the disc is pressed to close off passageway 101, which can be opened by backing off threaded stem member 57' or by rupturing diaphragm 39', to allow venting of gas through passageway 105, in a manner like that described with respect to the closure of FIGS. 1, 3 and 4. After venting, the container may be resealed, using the same rupture diaphragm. Thus, the container 11' is still protected by a rupture diaphragm against excessive pressures and can be vented by an operator by unscrewing threaded stem 57', which is like stem 57 of FIGS. 1, 3 and 4. The adapter also includes a tapping passage 107 which is always in communication with the interior of the container and which transmits the pressure of such interior to line 83 and thence to the monitor and/or controller 81.

Figure 8:
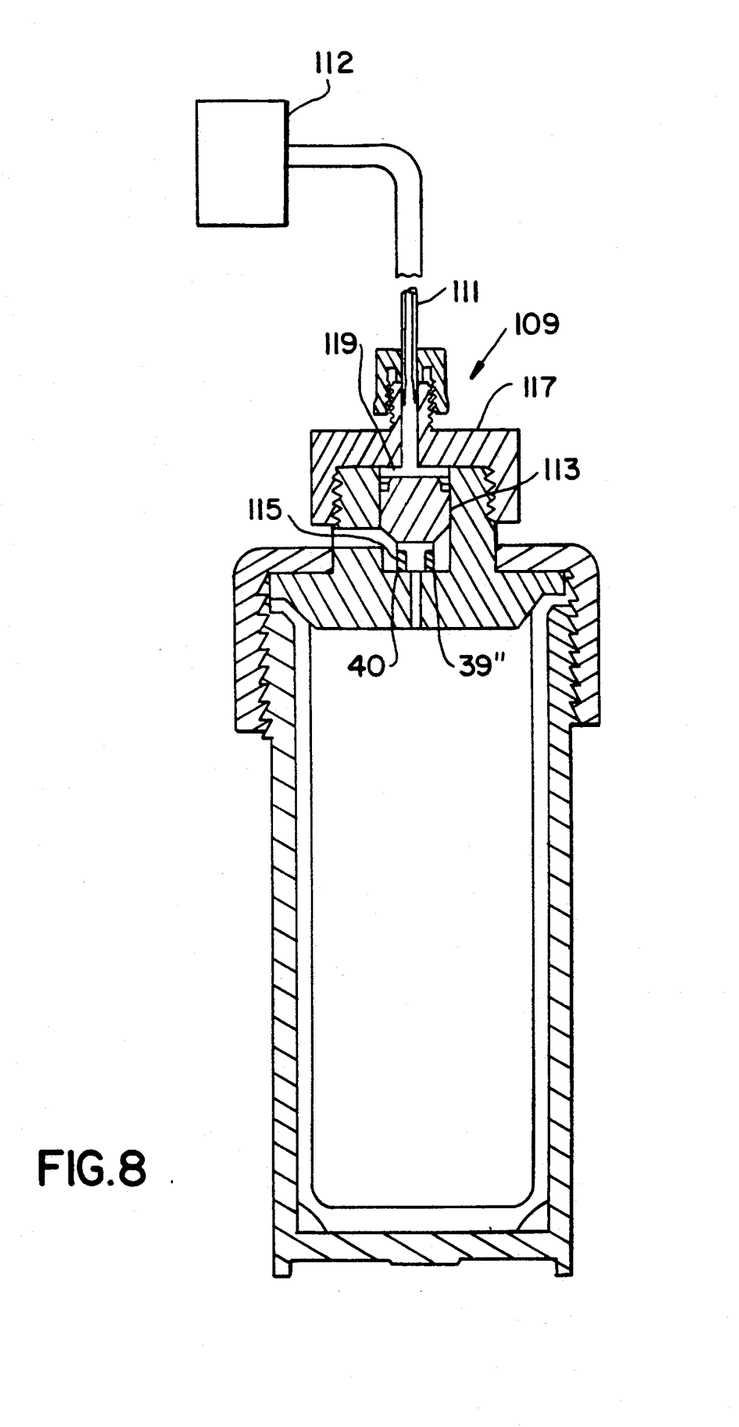
FIG. 8 is a central vertical sectional elevational view of the invented container of FIG. 1, except for the special sealing construction, and with a fluid pressure operated means for holding the rupture diaphragm in place.

FIG. 8 is essentially like FIG. 1, but with piston means 109 replacing threaded stem 57 for holding rupture disc 39" against its seat 40. As is seen, fluid pressure tube 111, which communicates with controllable pressure source 112, forces piston 113 downwardly, pressing contacting ring 115 against rupture disc 39". Screw cap 117 holds the piston means assembly together and the cap and the piston top 119 limit the piston's upward travel and thereby limit the travel of disc 39".

The advantages of this construction is that the pressure on the diaphragm may be automatically controlled by a programmed controller so as to release the diaphragm from its seat when the container reaches certain temperatures or certain pressures, or at certain times, without the need to rupture the diaphragm. However, the diaphragm, in place, protects against any possible malfunction of the controller unit. This construction also allows various programmed venting sequences, which may be according to predetermined schedules or in response to container conditions, or both.

Materials of construction of the various parts of the invented digestion container have already been described in some detail with respect to those parts suitable for the strengthening body portions and the liners. Suffice it to say that the body portion should give sufficient strength so as to withstand any normal pressures expected to be encountered during the digestion operation and the liner should be chemically resistant to the reagents and test materials being employed. In other words, any part which might contact the digesting liquid should be inert to it, and it is also desirable for other parts to be chemically inert. When it is desirable to be able to view the digesting material during digestion and when the digestion can be effected at comparatively low pressure, less than 7 kg./sq. cm. gauge, for example, the normally opaque reinforcing or strengthening body may be omitted and the clear or translucent liner or chemically resistant body part may be joined to the closure. However care should be exercised not to exceed the liner's safe limiting pressure and the liner should be protected by a rupture disc The capacity of the container can be such as is required for particular digestions but normally will be in the range of 50 to 200 ml., such as 75 to 150 ml. or about 100 ml., and the digestion mixture will normally be from 5 to 25% of such volume, e.g., about 10 to 20% thereof. Because digestions proceed faster at higher temperatures, with resulting higher pressures, it has been found to be desirable to increase such pressures (and corresponding equilibrium temperatures) so that the pressures are in the range of 5 to 35 kg./sq. cm., preferably 7 or 14 to 21 kg./sq. cm., and more preferably 14 to 21 kg./sq. cm.

The rupture diaphragm utilized, which is preferably of polyfluoroethylene, such as Teflon or Fluorocarbon PFA (TP) or PTFE(TP), e.g., Teflon 310 or 340, so as to rupture a desired pressure, normally in excess of 21 kg./sq. cm. gauge (and sometimes in excess of 35 kg./sq. cm. gauge) will normally be of a thickness in the range of 100 to 500 microns, preferably 125 to 250 microns. While the rupture diaphragm will preferably be disc-shaped, it may be of other suitable shapes, too. The venting passageway downstream of the rupture diaphragm determines the force applied to the diaphragm to rupture it because such force is the product of the upstream pressure and the area of the downstream passage and the diaphragm is held tightly in position against the seat up to the passageway by the end of the threaded stem. It has been found that the downstream passageway should normally be of an area in the range of 1 to 20 sq. mm., preferably 2 to 10 sq. mm., e.g., of a diameter of about 3 mm., when circular in cross-section. The upstream passageway will normally be less than or equal in cross-sectional area to the downstream passageway, e.g., about one-half such area. Preferably both passageways will be cylindrical (although other cross-sectional shapes are also operative).

The microwave apparatus employed will normally generate microwaves of a frequency of about 2.45 gigahertz and the power of the apparatus will usually be in the range of 500 to 1,000 watts, e.g., about 600, 750 or 900 watts. Such an apparatus is normally microprocessor controlled so that various sequences of heatings and different power deliveries can be selected.

In use, the described apparatus will be employed for digesting various types of materials in solubilizing reagents, such as strong oxidizing acids, e.g., nitric acid, and other strong acids, such as sulfuric and hydrochloric acids. If alkaline reagents are to be employed the materials of construction of the various parts of the container and accessories will be selected accordingly. Among the various materials that may be digested there may be mentioned animal tissues, e.g., bovine liver, fuels and lubricants, e.g., heating and motor oils, vegetable matter, nuclear material, wastes, sediments, ores, sewage sludges and foods.

The sample to be digested is weighed into the vessel (or the liner if a lined vessel is employed, as is preferred), after which the digesting reagent is added. With a Teflon PFA liner and a suitable polyether imide strengthening body member temperatures of 200° to 300° C. are obtainable at pressures in the range of 14 to 21 kg./sq. cm., without damaging the equipment. After assembly of the container with the digestable material and reagent in it, it is placed on the turntable and the turntable is started to rotate in alternating mode (oscillation). Usually the rotational speed will be in the range of 1 to 20 revolutions per minute with the oscillations being such that the turntable moves no more than 360° in either direction. The time of digestion is that which is required under the conditions but by the method of this invention it will normally be shorter than for other microwave digestions, usually being in the range of 1 to 60 minutes or 2 to 15 minutes, e.g., about 5 to 8 minutes at a temperature in the range of 100° to 300° C., preferably 200° to 300° C., e.g., 210°, 220° and 260° C. In some cases the venting means on the container will not be utilized during the digestion but will be employed after completion of the digestion, when it is desired to remove the digested material from the container. Such venting after digestion speeds up the whole operation because it is not necessary to cool the container down to atomspheric pressure before opening it. During the venting operation the restricted passageway, shown at 41 in the drawing, slows the venting of gas, which helps to prevent any entrainment of liquid with it, thereby protecting the microwave apparatus against being damaged by such hot and corrosive liquid material.

In addition to the manual venting of the container after completion of digestion, it may also be vented during the digestion process at appropriate times. Sometimes this is desirable to remove reaction products, which removal helps to force the reaction (digestion) and at other times it may be desirable to avoid venting and to maintain internal pressure in the container, so long as it is not excessive, which extra pressure helps to raise the equilibrium temperature of the digestion mix and thereby promotes faster digestion. Ventings by use of the present containers are readily controllable and even at high pressures venting during the digestion can be effected controllably and without any losses of the samples being digested. With the use of the pressure and/or temperature monitors and controllers, as previously described, optimum sequences of heatings and ventings may be effected automatically, or such operations may be conducted manually, utilizing the described apparatuses. In some circumstances, as when nuclear materials are being treated, robots may be employed to handle them and to operate the microwave apparatus and the venting means for the digestion container.

The following examples illustrate but do not limit the invention. Unless otherwise indicated all temperatures are in °C. and all parts are by weight in these examples, this specification and the appended claims.

EXAMPLE 1

Utilizing the digestion container illustrated in FIG. 1, with a pressure monitor (and sometimes a pressure or temperature controller, too) connected to it by means of an adapter like that shown in FIG. 7, different standard digestable materials were digested with strong reagents to test the capabilities of the present invention. In such digestions the digestion container, with a sample inside, was placed on a turntable in a CEM Corporation MDS-81-D microwave digestion apparatus, with the power set at about 170 watts, and with the turntable being in oscillating mode, rotating 360° at three oscillations per minute, and with the apparatus fan being set at maximum speed, for most effective exhaustion of any gases that might be released from the container. Several digestions of bovine liver (National Institute of Standards and Testing [N.I.S.T.] No. 1577a) were effected, utilizing different digestion conditions, sample weights and amounts of water, and in all such cases the digestions were successful, with clear yellow solutions resulting after short digestion times (usually less than ten minutes). During some such digestions the temperatures of the digesting mixes exceeded 200° C., and in some instances rose to 260° C., with pressures rising to the range of 7 to 21 kg./sq. cm., e.g., 16 or 17 kg./sq. cm., within ten minutes of the beginning of the digestion operation.

The digestion container employed was of polyfluoroethylene (Teflon 340), as were the closure parts, except for the rupture diaphragm, which was of Fluorocarbon PFA. The liner of approximately 150 ml. capacity, was approximately 11.3 cm. high, outside measurement, with the bottom and side walls thereof being about 2 mm. thick, and was 3.8 cm. in inside diameter. The strengthening body portion or casing was of Ultem polyether imide and was about 12 cm. tall, with bottom and side walls being about 3 mm. thick. Its inside diameter matched the liner outside diameter. The rupture diaphragm was circular, about 8 mm. in diameter and about 130 microns thick. The downstream and upstream venting passageways were circular in cross-sections, with the downstream passageway being about 2 mm. in diameter and the upstream passageway being about 1.5 mm. in diameter. After addition of the test specimen to be digested, and the reagent (70% nitric acid, diluted in some cases with water) the container was sealed by applying tightening hand pressure to the tightening ridges thereon, with the applied torque being approximately 60 kg. cm.

When 0.1 g. of the sample and 5 ml. of 70% nitric acid were used the internal pressure rose to about 10 kg./sq. cm. after ten minutes and in that time digestion was complete. In another run, when 0.25 g. of the sample was digested with 5 ml. of 70% nitric acid, using the same vessel and the same power input, the pressure rose to about 13 kg./sq. cm. after ten minutes and the digestion was also satisfactory. Because it had been noted in other experiments that sharp pressure increases were sometimes obtained even after a pressure controller had turned the microwave magnetron off, the next run (with 0.5 g. of sample) was modified by diluting the tric acid (5 ml.) with water, 2.5 ml. in one experiment and 5 ml. in the other, in successful efforts to prevent such out of control reactions. With the greater dilution by water the pressure reached about 15 kg./sq. cm. after ten minutes and with the lesser dilution it reached about 16 kg./sq. cm. after the same time. In all the runs reported herein the digestion liquid was clear yellow and resulted in a clear solution after dilution with water to 50 ml., indicative of satisfactory and complete digestion.

The above described procedure, utilizing 0.5 gram of sample, 5 ml. of 70% nitric acid, and 2.5 ml. of water, was followed in digesting U.S. Environmental Protection Agency Metal and Fish Standard No. 2227, N.I.S.T. Pine Needles No. 1575 and S.R.M. Citrus Leaves No. 1572. In all such cases the water was added to the nitric acid to prevent a runaway or rapid reaction, which otherwise could cause the rupture disc to rupture and relieve the container pressure, resulting in some losses of the samples. The digestions of such materials, under the same conditions as described for the bovine liver digestions, were successful, with the sample materials being completely dissolved and with the digestion liquid being soluble in water. In Test No. 2227 the pressure reached 19 kg./sq. cm. after ten minutes, in Test No. 1572 it reached 16 kg./sq. cm. after ten minutes, and in Test No. 1575 it reached 17 kg./sq. cm. after ten minutes.

In the mentioned runs the proportion of sample to $HNO_3$ was from 0.1 to 3.5 to 0.5 to 3.5 or 2.8 to 14.3%.

In all the previously mentioned successful digestions the rupture diaphragm held and no venting was employed until completion of the digestion, at which time the vessel was cooled to approximately room temperature in an ice bath and any remaining internal pressure, such as about 1 kg./sq. cm., was relieved by venting the container by turning the venting stem to allow the rupture diaphragm to move away from its seat a short distance, e.g., about 1 or 2 mm. Venting effected was quiet and controlled, with no losses of any of the digested materials.

The same venting diaphragm was employed for all the described runs but because of possible strains to which the diaphragms may be subjected in use and because of their low cost it will usually be desirable to employ new diaphragms for each run. Also, diaphragm release pressures can be regulated by using different diaphragm thicknesses and by modifying the downstream venting passageway size. For example, when the thickness of such a diaphragm is 130 microns and the downstream venting passageway is 3 mm. in diameter the rupture pressure is about 11 kg./sq. cm. and when the diaphragm is of Fluorocarbon PFA(TP), e.g., Teflon 310, the thickness is 250 microns and the downstream passageway is 3.2 mm. in diameter the rupture pressure is about 20 kg./sq. cm. One may obtain still higher rupture pressures, over 21 kg./sq. cm., by utilizing a PFA 340 Teflon membrane of 250 microns thickness or of 380 micron diameter, respectively. However, it should be kept in mind that the rupture diaphragm material, although chemically resistant to the digesting reagent, is susceptible to weakening with time under pressure and at elevated temperature, so such behavior should be taken into account in choosing the material of the diaphragm, its thickness, and the size of the downstream passageway adjacent it.

Although it is an object of the present invention to conduct the digestion process without causing the rupture membrane to rupture and release contents thereof into the microwave digestion apparatus, in some of the described processes, such as those wherein 70% nitric acid is employed as the digesting agent with certain samples and without dilution by water, runaway digestion reactions have caused sudden increases in internal pressures beyond those for which the equipment was designed, and in such cases, at pressures of about 11, 23 and 36 kg./sq. cm., the rupture diaphragms have ruptured and permitted pressure release by discharging gaseous contents of the container through the venting passageway. Such discharges were comparatively quiet and controlled and did not result in substantial damage to the equipment. When such internal pressures were exceeded without pressure relief the container exploded and the contents seriously damaged the microwave apparatus and endangered nearby personnel. It was noted that upon venting pressure release due to diaphragm rupture the liner sometimes distorts somewhat, with the sides being moved inwardly. However, this does not prevent it from being used in other digestions and when so employed it resumes its initial shape soon after being put under pressure.

The above processes were conducted with single containers in the apparatus turntable, ventings were to the interior of the microwave apparatus chamber and the discharge was almost entirely in gaseous state so no harm was done to the apparatus. However, for additional safety, the digestions are also run with venting connections carrying the vented gas and any entrained materials to collecting containers, such as that illustrated in FIG. 6 and identified by numeral 89. Also, when a plurality of digestions is to be run, up to ten or more of the described digestion containers may be employed and preferably venting tubes from each of them will be connected to such collecting container. Also, by utilizing an adapter, such as that illustrated in FIG. 1 the pressure (or temperature) in a typical digesting container is transmitted to a monitor/controller, such as that identified by numeral 81 in FIG. 5, which can be programmed to regulate the microwave power delivered by a magnetron and can also be programmed to vent the containers at certain times and/or pressures, by unscrewing threaded stems 57 (and 57') or by lowering pressures on fluid powered piston equivalents of such threaded stems, which also press the rupture diaphragm against the seat to close off the venting passageway.

EXAMPLE 2

Used motor oil samples N.I.S.T. No. 1084 and S.R.M. No. 1085 were digested, in separate operations, utilizing 0.5 g. each of sample and 10 ml. of 70% nitric acid, with the digesting containers being the same as described in Example 1. However, pressure controllers, like that described in FIGS. 5-7, were utilized. In initial runs the controllers were set to halt microwave heating when the pressure reached 5 kg./sq. cm. (all readings in these examples are gauge readings) and the microwave apparatuses were programmed for ten minute heatings at 170 watts. However, after about 4.3 minutes the pressure controllers shut off the magnetrons and thereafter, even without additional microwave energy being supplied to the digestion mixes, the internal pressures rose to about 14 kg./sq. cm. in less than a minute. The rupture diaphragms did not rupture and the containers were not automatically vented. The containers were manually vented by unscrewing of the venting stems after ten minutes (backing them off about 1 mm.) and were then resealed. The pressure controllers were set for 9 kg./sq. cm. and the microwave apparatuses were set for 15 minutes heating at 225 watts, followed by five minutes at no power. After completions of these programs the vessels were again manually vented and resealed. The pressure controllers were next set for 13 kg./sq. cm. and the microwave apparatuses were programmed for 15 minutes at 300 watts and five minutes at zero power. After completions of these third cycles the vessels were allowed to cool to room temperature, were manually vented and the acids were diluted to 100 ml. with water. It was noted that before such dilutions all of the acids initially charged was still present in the containers. It was concluded that the digestions were very successful, as evidenced by the facts that the diluted digestion mixes were clear solutions, and none of the reagents had been lost.

Used motor oil samples are difficult to digest and by means of the present process the digestion time has been reduced considerably, compared to open digestions and lower pressure closed digestions. Also, such digestions often result in digestion liquids which produce precipitates on dilution, indicating that such digestions are notas satisfactory as those of the present invention.

EXAMPLE 3

In a four-step process a sample of residual oil, S.R.M. No. 1634b, was digested by a process of this invention. 0.5 Gram of the sample was weighed into the same type of vessel described in Examples 1 and 2, 15 ml. of 70% nitric acid were added, the digestion container was sealed and the pressure controller was set at 5 kg./sq. cm. The magnetron was then turned on at 175 watts for ten minutes, after which the digestion container was manually vented in the manner previously described and was resealed. The pressure controller was then set for 6 kg./sq. cm. and the vessel was heated by 235 watts of microwave power for ten minutes, after which it was cooled for five minutes under no power, and was vented and resealed. The pressure controller was next set for 9 kg./sq. cm. and the digestion container was heated at 250 watts for 15 minutes, cooled by cutting the magnetron power off for five minutes, manually vented and resealed. In the fourth stage the pressure controller was set for 13 kg./sq. cm. and the vessel was heated at 250 watts for 15 minutes, cooled to room temperature and manually vented. The sealing cap was removed and water was poured into the liner to increase the volume of the liquid therein to 100 ml. Prior to dilution the solution was a clear yellow but on dilution white solids were precipitated which were filtered off. The remaining solution was ready for analysis.

Although the described digestion took longer than the desired 10 to 15 minutes (sometimes the invented digestions take as much as an hour) residual oil is very difficult to digest and even an hour's digestion time is considered to be an outstanding achievement. When lower pressure and open digestions are attempted it is found that even after over four hours there will still be black oily material left in the digestion vessel, showing that the digestion is incomplete. The present standard method for effecting such low pressure or open digestions is to utilize a mixture of sulfuric and nitric acids as the digesting acid in a closed vessel (at lower pressure than utilized in the present process), followed by open vessel digestion in a glass beaker in which the sample is heated until the sulfuic acid fumes, after which it is treated with 30% hydrogen peroxide. Such standard procedure takes considerably longer than the invented procedure described above, requires transfer of the sample between different vessels, and leaves the open sample subject to possible contamination during processing.

Various advantages of the present articles, apparatues, accessories and processes have been referred to previously but some of those, together with other advantages, will be noted here. First, the present invention permits an economy of construction by also utilizing a rupture diaphragm as a valve part, which may be moved to open a venting passageway of a container or a piece of apparatus. Because the rupture membrane still functions as such and also functions as a removable closure for venting purposes, only one venting passageway is needed, a usual valve part can be omitted, the valve structure can be made smaller and more economically, and fitting of such parts into a microwave digestion apparatus can be more easily effected. The described containers are readily resealable after venting and the rupture diaphragm is maintained in position adjacent the seat for it, so it can be resealed after venting without any special operations being required. In other words, even after venting, the chamber, in which the rupture diaphragm is present, is small enough to limit the "play" of such diaphragm so it cannot be twisted, biased, wrinkled or otherwise distorted prior to resealing. Neither can the rupture diaphragm be lost by being carried through the venting passageway with the venting gas.

The microwave heating of the polar digestion mixture allows direct heating of such mixture without the need to transfer heat through container walls, which will require such walls to be at even higher temperatures than in the present processes, thereby further softening or weakening them. The fact that digestion reagents are polar promotes good absorption by them of the microwave radiation. Also, high temperature (and high pressure) operations promote quicker digestions, saving chemist and operator time, which makes the invention of significant importance to the analytical community. In such pressure operations, although the rupture diaphragm can be so designed as to be ruptured at pressures in the range of 7 to 35 kg./sq. cm., e.g., 7 to 21 or 14 to 21, the design will be such that it will rupture at a safe pressure within such a range (under the applicable temperature and other conditions), and thereby will protect the various parts of the container and the microwave apparatus from significant damage that could otherwise occur due to explosion of the container if such a pressure is exceeded. Normally the rupture membrane will be set to rupture at a pressure within 1 to 3 kg./sq. cm. of and lower than the explosive pressure and usually it will also be such above the maximum desired operating pressure for the digestion reaction.

The invention and the processes described in the previous working examples may also be applied to heating or reacting materials, in addition to digesting them, and unlined vessels and processing equipment may also be protected by the ventable rupture diaphragm assembly. However, lined containers are highly preferred. An advantage of such lined containers that is very significant to analytical chemists is the easy pourability of the digested materials from the lined containers. After venting on completion of the digestion, and removal of the sealing collar and closure, the flanged liner facilitates easy pouring of the contents from it without the need to remove the liner from the strengthening body member. Also, in pouring from the liner, due to the liner flange overlapping the strengthening body neck, the contents do not contact the material of such strengthening body, which is less resistant to damage by the strong acid employed, and the nature of the polyfluoroethylene polymer also discourages flowing of the digested liquid down the side of the liner. Similarly, the digestion mixture is not contaminated by contact with the external parts of the container.

The invented adapter, which includes rupture means, venting control and pressure transmitting means, allows the invented container to be vented according to a timing program or according to internal pressure or temperature that is developed. The pressure passageway in the adapter, which communicates with the monitor/controller, can also be employed to carry temperature indicating means or an electrical signal to a temperature monitor/controller. Such controllers can operate the venting means of the adapter or of the other closures in a microwave apparatus to vent them at certain times or under certain pressure/temperature conditions, and times to such ventings can also be controlled. In one form, instead of the venting controlling means unscrewing the holding means, it may apply lesser pressures thereto, by means of fluid acutated members such as pistons, to promote ventings. Similarly, microwave radiation onto the containers can be controlled by such monitor/controllers. Thus, when handling extremely dangerous materials, such as radioactive materials or unpredictably reactive digestion mixtures, the operations of the present microwave digestion apparatus may be remotely controlled and may be carried out by robotic mechanisms in known manner, which needs not be described herein.

In pressurized reactions involving strong reagents it is extremely important to maintain pressure-tight seals (except at times when venting is desirable). The sealing aspect of the present invention has been described previously but in that description no details were given of the relationships of the coefficients of expansion of the body and liner materials employed. It is considered that for such coefficients of expansion to be sufficiently different, with the liner material coefficient being greater than that of the body material coefficient, in a distance equal to the length of the liner and its flange (about 11 cm.) the liner will tend to extend at least one mm. more than the body, say from 1 or 2 mm. to 8 mm. Such expansion will tightly press the liner against the closure and the strengthening body in the wedge shaped portion of the upper lip or flange, tightening the seal as the container is heated to operating digestion temperature. Differential expansions less than 1 mm. will have little effect on the seal and those in excess of 8 mm. would be expected to cause excessive distortion of the liner wall and the seal flange. The coefficient of linear thermal expansion for Ultem 1,000 resin is $5.6 \times 10^{-5}$ mm./mm./°C., whereas that for Teflon 340 is about $17 \times 10^{-5}$ mm./mm./°C. over the temperature ranges normally utilized (21° to 210° C.).

In the previous working examples variations in structures, materials, relationships and processing conditions may be made in accordance with the teachings in this specification and proportions of reagents may be varied $\pm 25\%$, while still staying within the ranges described in the specification, and the processes will still be operative.

The invention has been described with respect to various illustrative embodiments and working examples thereof but it is evident that it is not to be limited to these because one of skill in the art, with the present description before him, will be able to utilize substitutes and equivalents without departing from the invention.

What is claimed is:

1. A ventable container that is protected by rupture means against possible damaging effects of pressures higher than those for which the container was designed to be held at given temperatures, which comprises radiant energy transmissive container body means for holding material to be heated by radiant energy, which body means comprises an opening for addition and removal of said material, closure means for sealing said container opening, and venting means for venting gas from the container, which venting means comprises a passageway for gas being vented from the container, which passageway terminates in an outlet, rupture means, seating means for the rupture means, against which seating means the rupture means is held, to close the venting passageway, and means for controllably and releasably holding the rupture means against the seating means to seal off the venting passageway from the container body means when the rupture means is intact and is held against the seating means, and for venting the container through the venting passageway and outlet, when the intact rupture means is released from the seating means, in which occurrence and when the rupture means ruptures, vented gas exits from the container through the passageway outlet.

2. A container according to claim 1, wherein the container body means is microwave transmissive and has the opening therein at the top thereof, the radiant energy is microwave radiation, the releasable holding means contacts the rupture means and applies force to it to hold it against the seating means, and the closure means includes the venting means therein.

3. A container according to claim 2 wherein the container body means comprises a liner inside a strengthening container body, the liner, strengthening container body and closure means are held in sealing contacts by collar means which holds the closure means against the container body means, the closure means is resealable after ventings, and the venting means vents the container when the rupture means ruptures, and controllably vents it when the force holding such rupture means against the seating means is released or is overcome by pressure in the container so that the rupture means moves away from the seating means a controllable distance and opens the passageway for venting of gas from the container.

4. A container according to claim 3, in which the container, liner and strengthening container body are essentially cylindrical, with bottoms, and the strengthening container bottom has external threads thereon, on the exterior thereof, the closure means closes the opening at the top of the container body means and includes a boss that contains the means for releasably holding the rupture means against the seating means, and that contains at least a portion of the venting passageway, and the collar means is cylindrical and is internally threaded to screw onto external threads on the exterior of the strengthening container body.

5. A container according to claim 4 wherein the closure means comprises a fluid operated pressure means for pressing against the rupture means so as to press it against the seating means, which pressure means is connected to a source of controllable fluid pressure so that the maximum pressure in the container is limited by the pressure of the fluid pressure means.

6. A container according to claim 4 wherein the liner, closure means and rupture means are of chemically resistant polyfluoroethylene, the strengthening container is of a polyether imide synthetic organic polymer, and the container is suitable for heating contained material to elevated temperatures and to pressures in the range of 7 to 35 kg./sq. cm. gauge.

7. A container according to claim 4 wherein the liner material is of a greater coefficient of expansion than the material of the strengthening container body, the container body is vertical, the liner bottom contacts the interior of the bottom of the strengthening container body and the liner is tapered upwardly and outwardly between the top of the cylindrical wall thereof and the top periphery thereof, and the upper part of the strengthening container body and a bottom part of the closure means near the periphery thereof are shaped to match the liner at the top thereof, which shapes of the upper parts of the liner and strengthening container body, together with the closure means, make the seal between the liner, strengthening container body and closure means of increased tightness as the temperature of such parts rises, due to a greater expansion of the liner than the strengthening container body.

8. A container according to claim 5 wherein the closure means comprises threaded stem means for screwing into a threaded vertical bore in the closure means, into which the threaded stem means is removeably inserted, for pressing the rupture means against the seating means and for releasing the rupture means from contact with the seating means by backing off the threaded stem means.

9. A ventable container according to claim 1 wherein said container is positioned in a microwave apparatus chamber where it is subjectable to microwave radiation to heat polar contents of the container and digest such contents or materials in them.

10. A ventable container according to claim 1, wherein said container is positioned in a microwave apparatus chamber on a turntable therein, in the presence of at least one additional such ventable container, with venting outlets thereof connected to a collecting vessel from which venting gases are further vented.

* * * * *